United States Patent [19]

Sogabe et al.

[11] Patent Number: 5,298,411
[45] Date of Patent: Mar. 29, 1994

[54] GLUCOSE DEHYDROGENASE FROM PSEUDOMONAS

[75] Inventors: Atsushi Sogabe; Michiyo Minami; Yukihiro Sogabe; Shigenori Emi, all of Tsuruga, Japan

[73] Assignee: Toyo Boseki Kabushiki Kaisha, Osaka, Japan

[21] Appl. No.: 761,280

[22] Filed: Sep. 17, 1991

[30] Foreign Application Priority Data

Sep. 25, 1990 [JP] Japan .................. 2-256462

[51] Int. Cl.$^5$ ............................ C12N 9/04; C12N 1/20
[52] U.S. Cl. .............................. 435/190; 435/252.34; 435/874
[58] Field of Search ................ 435/190, 252.34, 874

[56] References Cited

U.S. PATENT DOCUMENTS

| | | | |
|---|---|---|---|
| 3,956,337 | 5/1976 | Niwa et al. | 546/243 |
| 4,221,869 | 9/1980 | Vandecasteele et al. | 435/117 |
| 4,545,382 | 10/1985 | Higgins et al. | 435/180 |
| 4,683,198 | 7/1987 | Ishikawa et al. | 435/190 |
| 4,711,245 | 12/1987 | Higgins et al. | 435/25 |
| 4,877,733 | 10/1989 | Takahashi et al. | 435/190 |
| 4,929,551 | 5/1990 | Eguchi et al. | 435/106 |

FOREIGN PATENT DOCUMENTS 0098136 1/1984 European Pat. Off. .
2244762 9/1974 France .

OTHER PUBLICATIONS

Matsushita et al., Methods in Enzymology, vol. 89, pp. 149–154, 1982.
Lynch et al., Can. J. Microbiol., vol. 21, pp. 1560–1572, 1975.
Matsushita et al., Agric. Biol. Chem., 44(7), 1505–1512, 1980.
"Enzymatic v. Fermentative Synthesis: Thermostable Glucose Dehydrogenase Catalyzed Regeneration of NAD(P)H for use in Enzymatic Synthesis", Wong et al., J. Am. Chem. Soc. 1985, 107, 4028–4031.

Primary Examiner—David M. Naff
Assistant Examiner—Michael V. Meller
Attorney, Agent, or Firm—Leydig, Voit & Mayer, Ltd.

[57] ABSTRACT

A substantially purified glucose dehydrogenase is disclosed. The enzyme has activity at a temperature of from about 30° C. to about 65° C. at a pH of from about pH 6 to about pH 10 and has an optimum activity at a temperature from about 50° C. to about 60° C. at a pH of from about 8.5 to about 9.0. The enzyme is further characterized by retaining at least 90% residual activity after treatment at 50° C. for 15 minutes, being NAD or NADP dependent, having a molecular weight of about 101,000 daltons as determined by gel filtration using TSK gel, having an isoelectric point of about 4.5 by ampholyte isoelectric focusing, and having a specificity for at least $\beta$-D-glucose and 2-deoxyglucose. The preferred source of the enzyme is Pseudomonas sp. FH1227.

4 Claims, 4 Drawing Sheets

GLUCOSE DEHYDROGENASE FROM PSEUDOMONAS

BACKGROUND OF THE INVENTION

The present invention relates to a novel glucose dehydrogenase usable for glucose determination in clinical laboratory tests and to a method for producing same.

Promoted by the recent spread of clinical examinations, glucose dehydrogenases usable for glucose determination have been in great demand. In particular, development of a glucose dehydrogenase which is excellent in thermal stability is desired in the field of dry chemistry among the fields of clinical examinations.

Presently-available glucose dehydrogenases usable for clinical examinations are glucose dehydrogenase (EC1.1.1.47) derived from the genus Bacillus and glucose dehydrogenase (EC1.1.1.119) derived from the genus Cryptococcus. The former is an enzyme which catalyzes the reaction of $\beta$-D-glucose+NAD(P)$^+$→D-$\delta$-gluconolactone+NAD(P)H+H$^+$, and the latter is an enzyme which catalyzes the reaction of D-glucose+NADP$^+$→D-$\delta$-gluconolactone+NADPH+H$^+$. For use in clinical examinations, the glucose dehydrogenase (EC1.1.1.47) capable of using both NADP and NAD as a coenzyme is more preferable than the glucose dehydrogenase (EC1.1.1.119) capable of using NADP solely as a coenzyme.

Yet, every glucose dehydrogenase (EC1.1.1.47) presently available on the market is unstable to heat, and development of a glucose dehydrogenase superior in thermal stability as an enzyme for clinical examinations, particularly for dry chemistry, has been desired.

While the origin of the conventional glucose dehydrogenase (EC1.1.1.47) has been known to be various bacteria such as the genus Bacillus and animal livers (see *Koso Handobukku*, 9th ed., p. 19, Asakurashoten), an NAD(P)-dependent glucose dehydrogenase derived from the genus Pseudomonas has not been known. In addition, the known glucose dehydrogenase produced by the bacteria belonging to the genus Pseudomonas is an NAD(P) non-dependent glucose dehydrogenase (EC1.1.99.a) [Methods in Enzymology, vol. 9, 92-98 (1966), Agric. Biol. Chem., 44 (7), 1505-1512 (1980)] which is difficult to use in clinical fields.

SUMMARY OF THE INVENTION

The object of the invention is to provide an NAD(P)-dependent glucose dehydrogenase having high thermal stability, and a method for producing same.

DETAILED DESCRIPTION OF THE INVENTION

Figure 1:
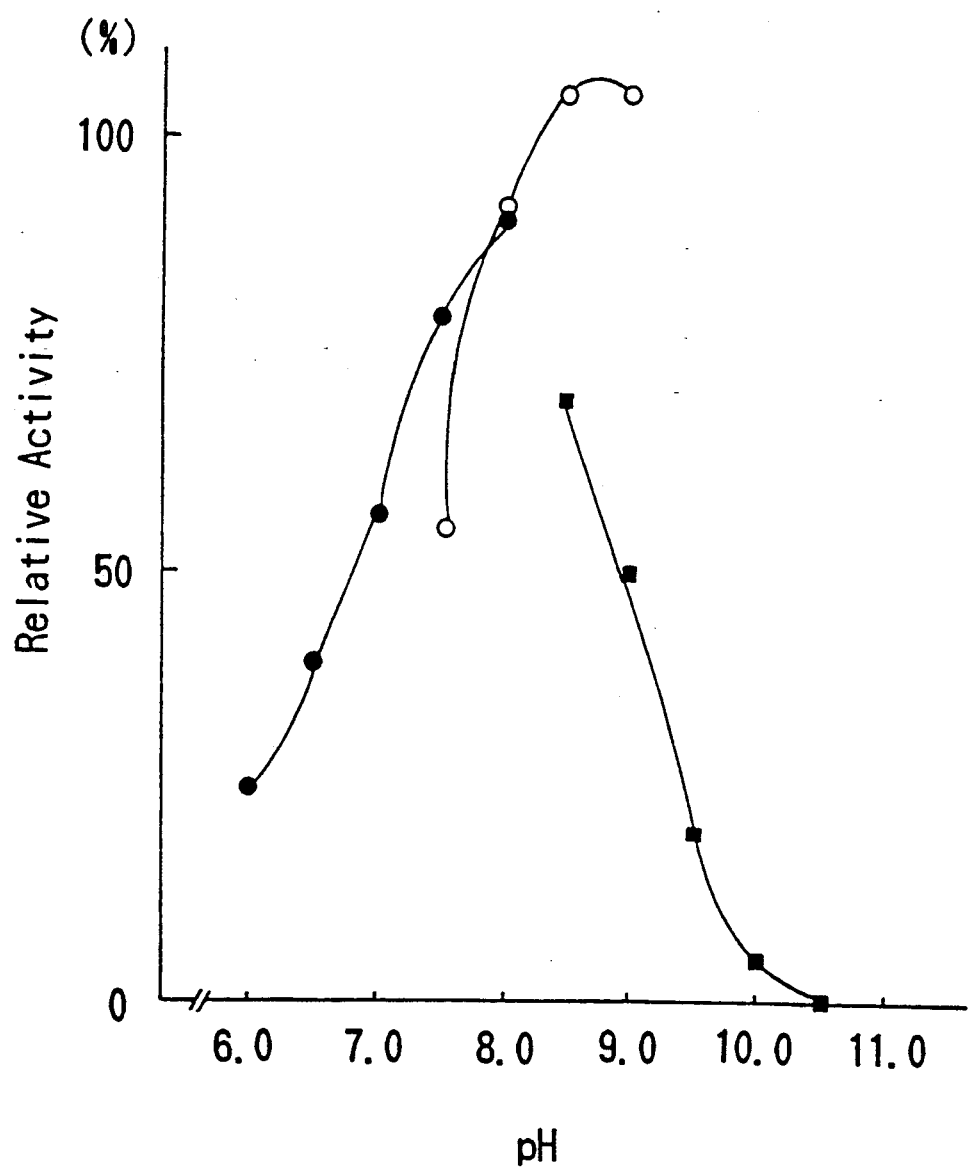
FIG. 1 shows relations between pH and activity of the glucose dehydrogenase of the invention, wherein ● (6.0-8.0) is phosphate buffer, ○ (7.5-9.0) is Tris-HCl buffer and ■ (8.5-10.5) is carbonate buffer.

The present invention provides a glucose dehydrogenase derived from the genus Pseudomonas, which catalyzes the following reaction, and a method of producing the glucose dehydrogenase, comprising culture of a bacterium capable of producing the glucose dehydrogenase derived from the genus Pseudomonas, which catalyzes the following reaction, and harvesting said glucose dehydrogenase from the culture.

$\beta$-D-glucose+NAD(P)$^+$→D-$\delta$-gluconolactone+NAD(P)H+H$^+$

Any strain belonging to the genus Pseudomonas can be used in the present invention, with preference given to the Pseudomonas sp. FH1227 strain belonging to the genus Pseudomonas, collected from the soil in Tsuruga-shi, Fukui, Japan by the present inventors.

Microbiological properties of the Pseudomonas sp. FH1227 strain mentioned above are as follows.

I. Morphological Properties

It is a bacillus having a size of 2.5×0.7 by culture at 30° C. for 20 hours in broth agar medium, which shows negative in Gram staining and has motility.

II. Growth in Various Media (1) broth agar plate culture

It forms a round colony with a diameter of 1-3 mm by culture at 30° C. for 24 hours. The surface is smooth and glossy, the upheaval is in thin, flat round, the colony is homogeneous, opaque and pale flesh in color, forming no soluble dye or fluorescent dye.

(2) broth agar slant culture

It grows well on the slant front by culture at 30° C. for 24 hours. The cell color is pale flesh.

(3) broth liquid culture

It grows well by shaking culture at 30° C. for 16 hours, but grows little by standing culture.

(4) broth agar stab culture

It grows well in the upper agar but grows poor at a depth by culture at 30° C. for 24 hours.

(5) growth temperature

It grows at a temperature between 25° C. to 42° C. by shaking culture in broth liquid medium, with the best growth at around 37° C.

(6) growth pH

It shows good growth at a pH between 6 and 8 by shaking culture in broth liquid medium.

III. Physiological Properties

| | |
|---|---|
| (1) nitrate reduction | positive |
| (2) denitrification | negative |
| (3) $\beta$-galactosidase | negative |
| (4) arginine dihydratase | negative |
| (5) lysine decarboxylase | negative |
| (6) ornithine decarboxylase | negative |
| (7) citrate utilization | negative |
| (8) hydrogen sulfide production | negative |
| (9) urease | negative |
| (10) tryptophan deaminase | negative |
| (11) VP test | positive |
| (12) gelatin decomposition | positive |
| (13) OF test | nonfermentative |
| (14) catalase | positive |
| (15) oxidase | negative |
| (16) acid formation from sugar | no formation from glucose, mannitol, inositol, D-sorbitoinositol, D-sorbitol, L- |

-continued

| | |
|---|---|
| rhamnose, saccharose, D-melibiose and D-amygdalin; formation from L-arabinose | |
| (17) dye formation | no formation of soluble dye, fluorescent dye |
| (18) against oxygen | aerobic |
| (19) Tween decomposition | negative |
| (20) need for vitamin or amino acid | no particulur need |

The experiment methods for the identification of microbiological properties mentioned above were in accord with *Biseibutsu no Bunrui to Doutei*, edited and authored by Takeharu Hasegawa, Gakkai Shuppan Center (1975). The standards for classification and identification were employed in reference to Bargey's Manual of Systematic Bacteriology, Vol. 1 (1984).

Based on the above literatures and various microbiological properties as described, the FH1227 strain is considered to belong to the genus Pseudomonas. In addition, the FH1227 strain coincides well with *Pseudomonas viridiflava* except dye formation. Thus, the present strain was named Pseudomonas sp. FH1227 strain, which has been deposited at the Fermentation Research Institute, Agency of Industrial Science and Technology, Ministry of International Trade and Industry, Japan under the accession number 11618.

In the present invention, any nutrient medium usually employed can be used. As the carbon sources, used are various monosaccharides including glucose, and various organic acids such as succinic acid and malic acid. As the natural nutrition sources, used are peptone, yeast extract, meat extract and so on, and as nitrogen sources, there may be used inorganic nitrogen sources such as ammonium sulfate and ammonium chloride.

As inorganic salts, there may be mentioned potassium phosphate, potassium chloride, sodium chloride and magnesium sulfate. These nutrition sources can be used alone or in combination.

The strain can be normally cultured by shaking culture or aeration spinner culture. Generally, culture temperature preferably ranges from 25° C. to 37° C. and pH of the medium is preferably in the range of 5.5–7.5. Generally culture for 18 to 24 hours produces and accumulates glucose dehydrogenase (EC1.1.1.47) in the cells. Culture conditions are naturally such that permits maximum production of the glucose dehydrogenase (EC1.1.1.47) according to strains and medium compositions to be employed. In harvesting the glucose dehydrogenase (EC1.1.1.47) produced and accumulated according to the present invention, cells are collected by centrifugation and filtration of the culture, and crushed by beads disintegration, ultrasonic disintegration, lytic enzyme treatment, or the like. It is desirable that the most efficient extraction method be employed according to the strains to be used. The glucose dehydrogenase (EC1.1.1.47) can be separated from the crude enzyme solution thus obtained by a method conventionally employed for enzyme purification. Examples of such method include polyethylene imine treatment, ammonium sulfate salting out isoelectric precipitation, ion exchange chromatography, gel filtration, hydrophobic chromatography and so on, which may be used in combination. For example, a crude enzyme solution is centrifuged to give a supernatant. Thereto is added polyethylene imine, thereby removing the nucleic acid, and a supernatant is obtained. The fraction (0.5–0.7 saturation) salted out with ammonium sulfate is obtained from the supernatant. The fraction is desalted and concentrated by Sephadex G-25 gel filtration, after which it is adsorbed on DEAE Sepharose CL 4B ion exchanger and eluted. The active fraction is adsorbed on Phenyl Toyopearl 650M and eluted. The active fraction is desalted by Sephadex G25 gel filtration and the active fraction is recovered to separate highly-purified glucose dehydrogenase (EC1.1.1.47).

Examples of physicochemical properties of the glucose dehydrogenase of the invention are as follows.

(1) Action

The enzyme of the invention produces 1 mole of D-δ-gluconolactone and 1 mole of NAD(P)H+ from 1 mole of β-D-glucose and 1 mole of NAD(P).

(2) Substrate specificity

As shown in Table 1 below, the enzyme of the invention specifically acts on β-D-glucose and 2-deoxyglucose.

TABLE 1

| Substrate (100 mM) | Relative activity (%) |
|---|---|
| β-D-glucose | 100.0 |
| L-glucose | 0.0 |
| xylose | 8.9 |
| 2-deoxy-glucose | 119.7 |
| L-sorbose | 0.3 |
| D-mannose | 2.4 |
| D-fructose | 0.8 |
| D-galactose | 0.1 |
| D-lactose | 1.2 |
| D-sorbitol | 0.1 |
| D-mannitol | 0.0 |
| saccharose | 0.0 |
| inositol | 0.2 |
| maltose | 3.9 |

(3) Optimum pH

The enzyme of the invention exhibits high activity at the pH range of 8.5–9.0 as shown in FIG. 1.

(4) Optimum temperature

Figure 2:
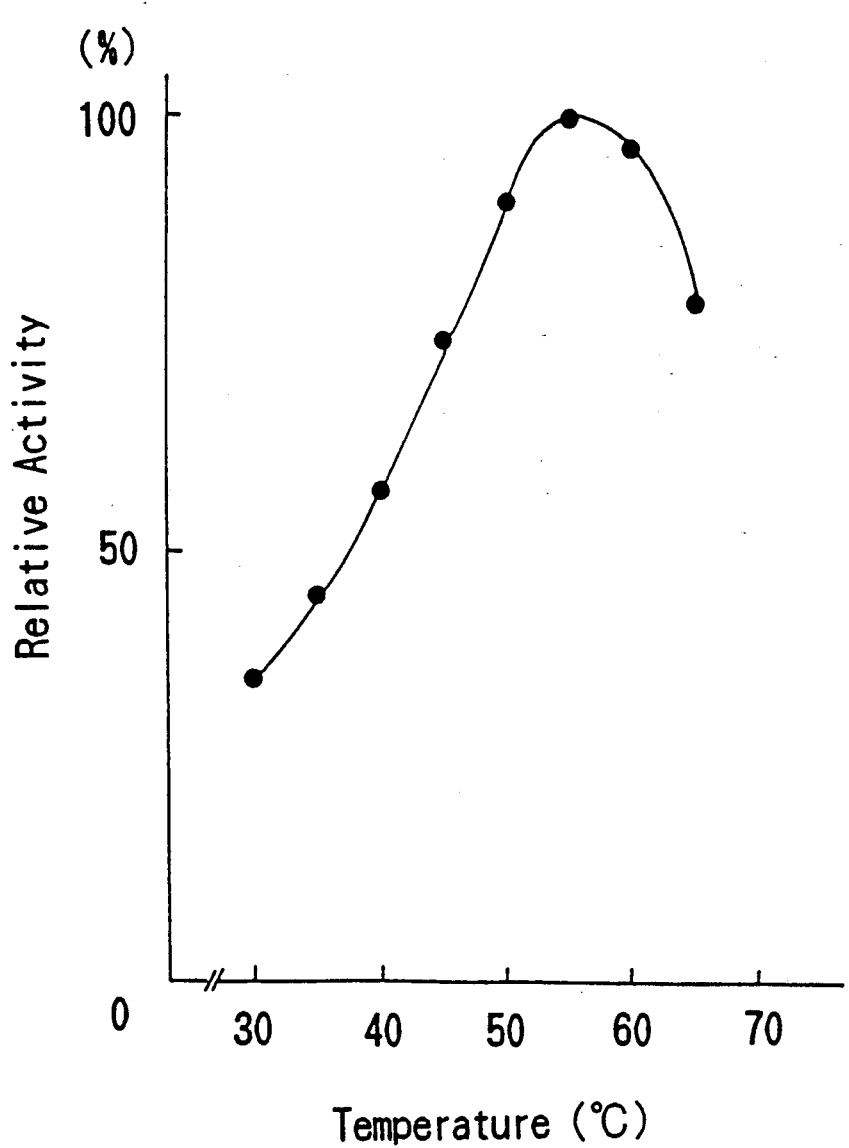
FIG. 2 shows relations between temperature and activity.

The optimum temperature of the enzyme of the invention is 55° C. as shown in FIG. 2.

(5) pH stability

Figure 3:
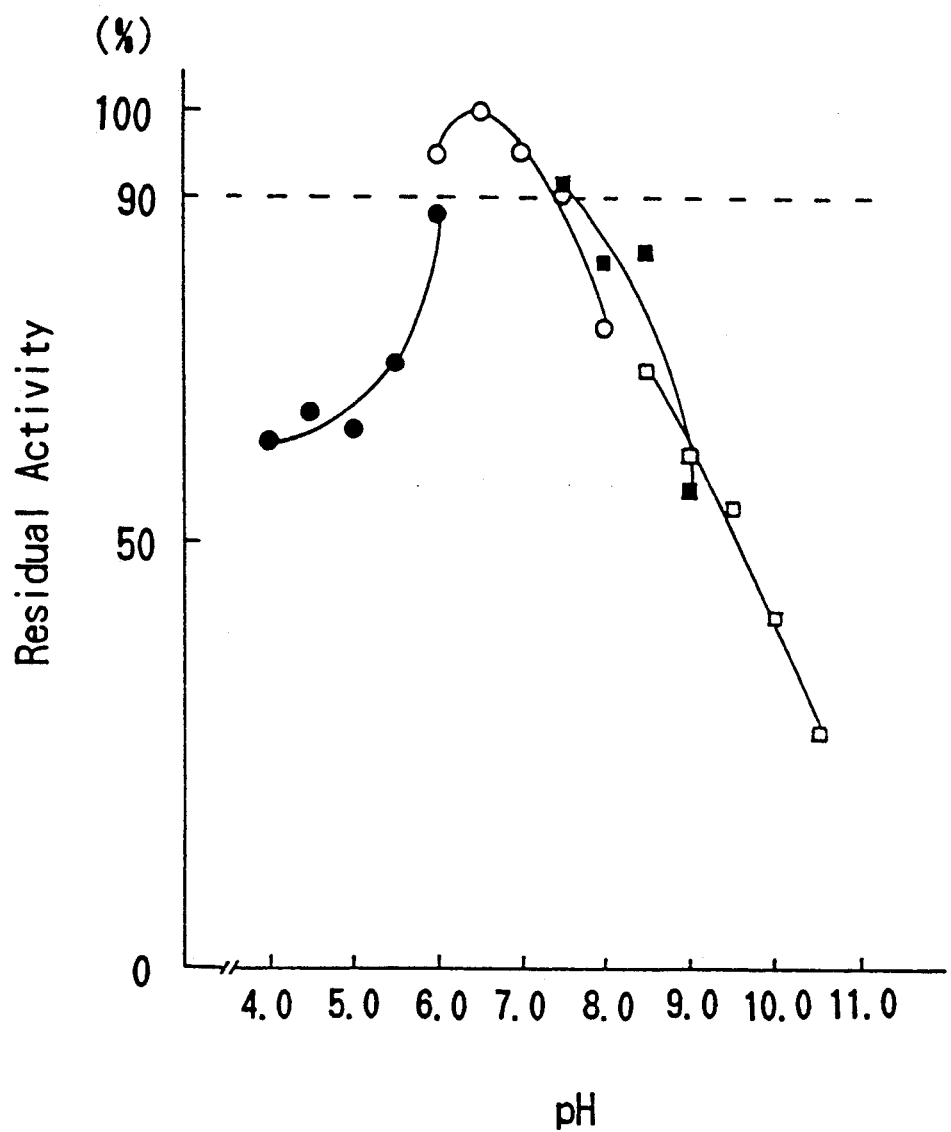
FIG. 3 shows relations between pH and activity upon 16 hours' treatment at respective pHs at 20° C., wherein ● (4.0-6.0) is acetate buffer, ○ (6.0-8.0) is phosphate buffer, ■ (7.5-9.0) is Tris-HCl buffer and □ (8.5-10.5) is carbonate buffer.

The pH stability upon 16 hours' treatment of the enzyme of the invention at 20° C. and at various pHs is given in FIG. 3. As is evident therefrom, the enzyme of the invention is stable at the pH range of 6.0–7.5.

(6) Thermal stability

Figure 4:
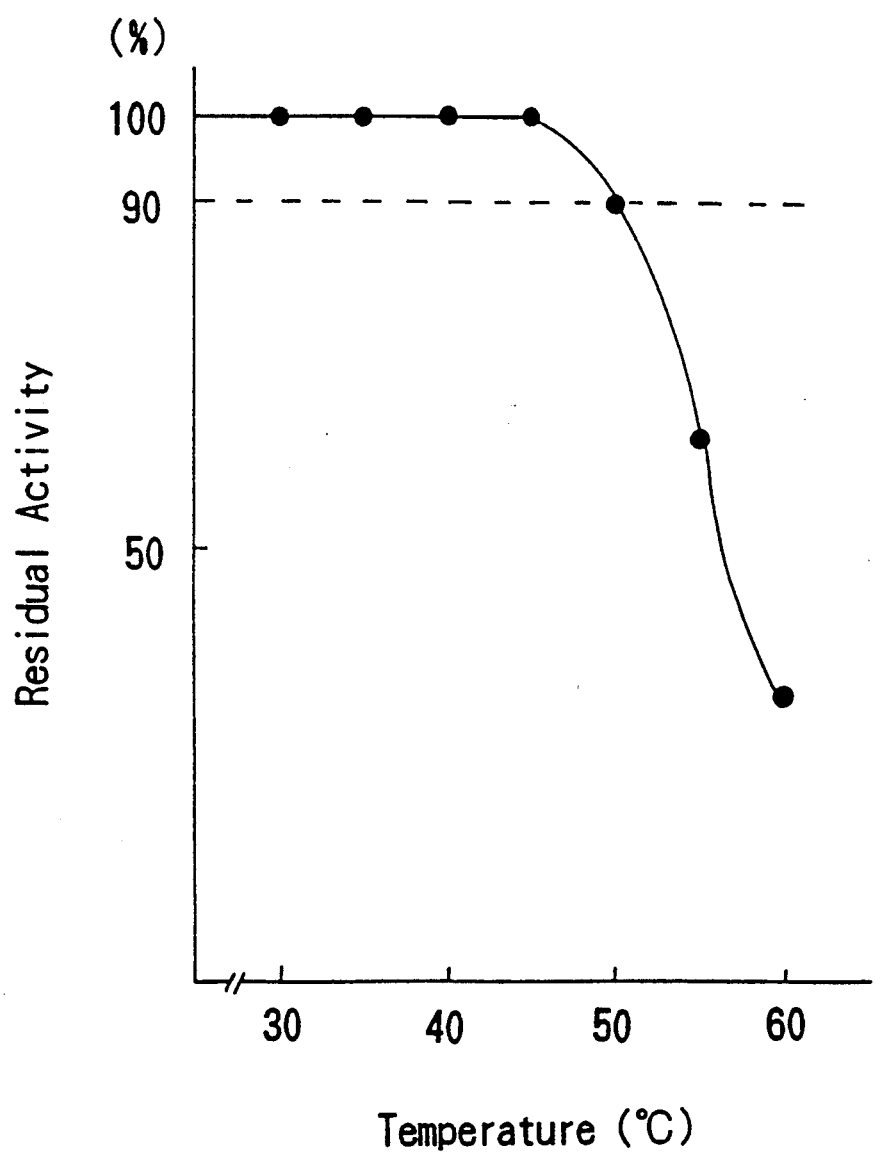
FIG. 4 shows relations between temperature and activity upon 15 minutes' treatment at respective temperatures at pH 7.0.

The thermal stability upon 15 minutes' treatment at pH 7.0 and at various temperatures is given in FIG. 4. As is evident therefrom, the enzyme of the invention is stable up to 50° C.

(7) Inhibitor

As shown in Table 2 below, the enzyme of the invention was inhibited by silver nitrate, mercury chloride and monoiodoacetate.

TABLE 2

| Inhibitor | Concentration | Relative activity (%) |
|---|---|---|
| non added | — | 100.0 |
| silver nitrate | $2.0 \times 10^{-3}$ M | 7.1 |
| mercury chloride | $2.0 \times 10^{-3}$ M | 5.9 |
| monoiodoacetate | $2.0 \times 10^{-3}$ M | 0.4 |

(8) Km value

The Km value of the enzyme of the invention to β-D-glucose is either $1.38 \times 10^{-2}$M (coenzyme NAD) or $1.25 \times 10^{-2}$M (coenzyme NADP), and the Km value to the coenzyme is $3.08 \times 10^{-4}$M (NAD) or $4.07 \times 10^{-5}$M (NADP).

(9) Molecular weight

The enzyme of the invention has a molecular weight of about 101,000 by gel filtration using TSK gel G3000SW.

(10) Isoelectric point

The isoelectric point of the enzyme of the invention is about 4.5 by ampholyte isoelectric focusing.

(11) Enzyme activity determination

The enzyme activity was determined by taking the enzyme activity producing 1 micromole of NADH per 1 minute under the conditions mentioned below as 1 unit.

Reagent:

(A) 0.1M Tris-HCl buffer, pH 8.0

(B) 1.5M D-glucose solution (prepared by dissolving 27.02 g of D-glucose in 100 ml of distilled water)

(C) 80 mg/ml NAD solution (prepared by dissolving 80 mg of NAD trihydrate in 1 ml of distilled water which is to be prepared when in use)

(D) Enzyme solution (prepared by diluting a standard enzyme to 0.8-1.2 U/ml with previously ice-cooled 50 mM phosphate buffer, pH 7.0)

Procedure:

1. The following reaction mixture is prepared in a cuvette (d=1 cm) and preheated at 37° C. for about 5 minutes.
   (A) Solution 2.6 ml
   (B) Solution 0.3 ml
   (C) Solution 0.1 ml 2. An enzyme solution (0.05 ml) is added thereto, and the mixture is gently stirred. The change of absorbance at 340 nm is recorded for 5 minutes using a spectrophotometer controlled at 37° C. with water as the control. The change of absorbance per 1 minute is estimated on the basis of the linear portion from minute 2 to minute 5. ($\Delta OD$ test)

3. The blank test is conducted by following the same procedure as above except that 0.05 ml of a diluted enzyme solution (with phosphate buffer, pH 7.0) is used in place of the enzyme solution, to estimate the change in absorbance per 1 minute. ($\Delta OD$ blank)

Calculation equation:

$$U/ml = \frac{\Delta OD/\min (\Delta OD \text{ test} - \Delta OD \text{ blank}) \times 3.05 \times \text{dilution}}{6.22 \times 1.0 \times 0.05}$$
$$= \Delta OD/\min \times 9.807 \times \text{dilution}$$

6.22 = millimole molar absorption coefficient of NADH ($cm^2/\mu M$)

1.0 = optical path length (cm)

Hereinafter, the glucose dehydrogenase of the invention is explained by way of examples. "%" means weight % (w/v) unless otherwise specified.

EXAMPLE 1

Composition of Medium A 1.0% glucose, 0.3% yeast extract, 0.3% polypeptone, 0.3% meat extract, 0.1% $KH_2PO_4$, 0.22% $K_2HPO_4$, 0.05% $MgSO_4.7H_2O$, pH 7.0

Composition of Medium B 1.0% DL-malic acid, 1.0% yeast extract, 0.3% polypeptone, 0.2% meat extract, 0.1% $KH_2PO_4$, 0.22% $K_2HPO_4$, 0.2% NaCl, 0.05% $MgSO_4.7H_2O$, pH 6.0

Medium A above (100 ml) was put in a 500 ml-Sakaguchi flask and sterilized in an autoclave at 121° C. for 15 minutes. One platinum loop of Pseudomonas sp. FH1227 (FERM BP-11618) was inoculated to Medium A above and subjected to shaking culture at 30° C. for 24 hours, which was used as a seed culture. Said seed culture (60 ml) was inoculated to Medium B (6 l) sterilized under the same conditions, in a 10 l-jar fermentor, which was cultured at 480 rpm, aeration 2 l/min, 30° C. and pH control 7.5 for 18 hours. The glucose dehydrogenase (EC1.1.1.47) activity of the culture obtained was 1.2 U/ml. The culture (6 l) was centrifuged, and the cells were collected and suspended in 50 mM phosphate buffer (pH 7.0). The suspension (1 l) was crushed by French Press disintegrator (Minilabo, Dainippon Pharmaceutical Co., Ltd.). To the solution containing the disintegrated cells were added polyethylene imine and 0.1M NaCl having the final concentration of 0.12%, and the mixture was gently stirred at room temperature for 15 minutes and left standing. The mixture was centrifuged to give a supernatant, to which ammonium sulfate was added in such an amount that makes the supernatant 0.5 saturation, and the mixture was centrifuged to give a supernatant. To the supernatant was added ammonium sulfate to make the supernatant 0.7 saturation, which was then centrifuged to give precipitate. The precipitate was redissolved in 140 ml of 50 mM phosphate buffer, pH 7.0. The redissolved solution was desalted by Sephadex G-25 column (1.5l) equilibrated with 50 mM phosphate buffer, pH 7.0. The desalted solution was adsorbed on DEAE-Sepharose CL-4B column (50 ml) and eluted with the 0-0.3M NaCl gradient. Ammonium sulfate was added to make the eluate 0.4 saturation, and the insoluble matter was separated by centrifugation to give a supernatant, which was then adsorbed on 10 ml of Phenyl Toyopearl 650M equilibrated with 50 mM phosphate buffer, pH 7.0 containing ammonium sulfate added for 0.4 saturation, and eluted with the 0.4-0 saturation ammonium sulfate gradient and the 0-10% ethylene glycol gradient. The eluate was concentrated by ultrafiltration and desalted with Sephadex G-25 column (100 ml) equilibrated with 50 mM phosphate buffer, pH 7.0 to give an active fraction. The relative activity of the active fraction was about 120 U/mg protein. The physicochemical properties of the glucose dehydrogenase thus obtained were as mentioned above.

The glucose dehydrogenase according to the present invention is an NAD(P)-dependent enzyme obtained from the genus Pseudomonas, which is stable to heat up to 50° C. and permits use of both NAD and NADP as a coenzyme, and is useful as an enzyme for clinical use.

What is claimed is:

1. A substantially purified glucose dehydrogenase, having activity at a temperature of from about 30° C. to about 65° C. at a pH of from about pH 6 to about pH 10, having an optimum activity at a temperature from about 50° C. to about 60° C. and at a pH of from about 8.5 to about 9.0, and retaining at least 90% residual activity after treatment at 50° C. for 15 minutes said glucose dehydrogenase being NAD or NADP dependent, having a molecular weight of about 101,000 daltons by gel filtration using TSK gel and having an isoelectric point of about 4.5 by ampholyte isoelectric focusing, and having a specificity for at least β-D-glucose and 2-deoxyglucose.

2. A glucose dehydrogenase according to claim 1 that is derived from Pseudomonas bacteria.

3. A glucose dehydrogenase according to claim 2 having a $K_m$ for β-D-glucose of (1) about $1.38 \times 10^{-2}$M in the presence of coenzyme NAD, and (2) about $1.25 \times 10^{-2}$M in the presence of coenzyme NADP.

4. A glucose dehydrogenase according to claim 2 having a $K_m$ (1) for coenzyme NAD of about $3.08 \times 10^{-4}$M, and (2) for coenzyme NADP about $4.07 \times 10^{-5}$M.

* * * * *